US00PP28025P3

(12) United States Plant Patent
Drewlow

(10) Patent No.: US PP28,025 P3
(45) Date of Patent: May 16, 2017

(54) POINSETTIA PLANT NAMED 'PER1295'

(50) Latin Name: ***Euphorbia pulcherrima* Willd.**
Varietal Denomination: PER1295

(71) Applicant: Lyndon Wayne Drewlow, Lompoc, CA (US)

(72) Inventor: Lyndon Wayne Drewlow, Lompoc, CA (US)

(73) Assignee: Dümmen Group B.V., De Lier (NL)

( * ) Notice: Subject to any disclaimer, the term of this patent is extended or adjusted under 35 U.S.C. 154(b) by 142 days.

(21) Appl. No.: 14/545,815

(22) Filed: Jun. 23, 2015

(65) Prior Publication Data

US 2016/0381850 P1 Dec. 29, 2016

(51) Int. Cl.
*A01H 5/02* (2006.01)

(52) U.S. Cl.
USPC ..... Plt./307

(58) Field of Classification Search
USPC ..... Plt./263.1, 302, 303, 307
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Poinsettia plant named 'PER1295', characterized by its uniform, upright and mounded plant habit; moderately vigorous growth habit; freely and upright branching habit; very dark green-colored leaves; early flowering response; large inflorescences with crimson-colored flower bracts; and good post-production longevity.

1 Drawing Sheet

Botanical designation: *Euphorbia pulcherrima* Willd.
Cultivar denomination: 'PER1295'.

BACKGROUND OF THE INVENTION

The present invention relates to a new and distinct cultivar of Poinsettia plant, botanically known as *Euphorbia pulcherrima* Willd., and hereinafter referred to by the name 'PER1295'.

The new Poinsettia plant is a product of a planned breeding program conducted by the Inventor in Lompoc, Calif. The objective of the breeding program is to create new compact Poinsettia plants with dark green-colored leaves, large inflorescences with dark red-colored flower bracts, early flowering response, good cyathia retention and excellent post-production longevity.

The new Poinsettia plant originated from a cross-pollination made by the Inventor in December, 2004 of a proprietary selection of *Euphorbia pulcherrima* Willd. identified as code number 03-149-4, not patented, as the female, or seed, parent, with a proprietary selection of *Euphorbia pulcherrima* Willd. identified as code number 04-277-1, not patented, as the male, or pollen, parent. The new Poinsettia plant was discovered and selected by the Inventor as a single flowering plant from within the progeny of the stated cross-pollination in a controlled greenhouse environment in Lompoc, Calif. in December, 2005.

Asexual reproduction of the new Poinsettia plant by terminal vegetative cuttings in a controlled greenhouse environment in Lompoc, Calif. since July, 2006 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER1295'. These characteristics in combination distinguish 'PER1295' as a new and distinct Poinsettia plant:

1. Uniform, upright and mounded plant habit.
2. Moderately vigorous growth habit.
3. Freely and upright branching habit.
4. Very dark green-colored leaves.
5. Early flowering response; under natural season conditions, plants flower in mid-November in Southern California.
6. Large inflorescences with crimson-colored flower bracts.
7. Good post-production longevity.

In side-by-side comparisons conducted in Lompoc, Calif., plants of the new Poinsettia differ primarily from plants of the female parent selection in flower bract shape and size as plants of the new Poinsettia have broader flower bracts than plants of the female parent selection. In addition, plants of the female parent selection shed pollen one week later than plants of the new Poinsettia.

In side-by-side comparisons conducted in Lompoc, Calif., plants of the new Poinsettia differ primarily from plants of the male parent selection in plant size as plants of the new Poinsettia are more compact than plants of the male parent selection. In addition, plants of the new Poinsettia had larger cyathia than plants of the male parent selection.

Plants of the new Poinsettia can be compared to plants of the *Euphorbia pulcherrima* Willd. 'Eckadire', disclosed in U.S. Plant Pat. No. 12,846. In side-by-side comparisons conducted in Lompoc, Calif., plants of the new Poinsettia differed primarily from plants of 'Eckadire' in the following characteristics:

1. Plants of the new Poinsettia was not as vigorous as plants of 'Eckadire'.
2. Plants of the new Poinsettia had darker green-colored leaves than plants of 'Eckadire'.
3. Plants of the new Poinsettia had darker red-colored flower bracts than plants of 'Eckadire'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'PER1295' grown in a container.

The photograph at the top of the sheet is a close-up view of a typical flowering plant of 'PER1295'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 24° C., night temperatures averaged 18° C. and light levels averaged 5,000 foot-candles. Measurements and numerical values represent averages for typical flowering plants. Plants were pinched one time and were 17 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER1295'.

Parentage:

*Female, or seed, parent*.—Proprietary selection of *Euphorbia pulcherrima* Willd. identified as code number 03-149-4, not patented.

*Male, or pollen, parent*.—Proprietary selection of *Euphorbia pulcherrima* Willd. identified as code number 04-277-1, not patented.

Propagation:

*Type*.—Terminal vegetative cuttings.

*Time to initiate roots*.—About seven to ten days at 20° C. night temperature and 27° C. day temperature.

*Time to produce a rooted young plant*.—About four weeks at 20° C. night temperature and 27° C. day temperature.

*Root description*.—Fibrous; white in color.

Plant description:

*Plant habit and form*.—Uniform, upright and mounded plant habit; inverted triangle; large inflorescences positioned above the foliar plane; moderately vigorous growth habit.

*Plant height*.—About 38 cm.

*Plant diameter or spread*.—About 56 cm.

*Lateral branch description*.—Quantity: Freely branching habit, about six lateral branches develop after pinching. Length: About 32 cm. Diameter: About 7 mm. Internode length: About 2 cm. Strength: Strong. Texture: Smooth, glabrous; luster, somewhat glossy. Color: Close to 146A.

*Leaf description*.—Arrangement: Alternate, simple. Length: About 10.8 cm. Width: About 7.4 cm. Shape: Lanceolate. Apex: Acuminate. Base: Rounded to nearly truncate. Margin: Entire; not lobed. Aspect: Flat. Venation pattern: Pinnate, arcuate. Texture, upper surface: Sparsely pubescent. Texture, lower surface: Pubescent. Color: Developing leaves, upper surface: Darker than 139A. Developing leaves, lower surface: Close to 137A. Fully expanded leaves, upper surface: Darker than 139A, almost black; venation, close to 146B. Fully expanded leaves, lower surface: Close to 137B; venation, close to 147C. Petioles: Length: About 5.4 cm. Diameter: About 3 mm. Texture, upper and lower surfaces: Smooth, glabrous. Color, upper surface: Close to 187B. Color, lower surface: Close to 183B.

Inflorescence description:

*Inflorescence type and habit*.—Terminal inflorescences are compound corymbs of cyathia with colored flower bracts subtending the cyathia; inflorescences uniformly positioned above the foliar plane.

*Fragrance*.—None detected.

*Flowering response*.—Early season flowering response; under natural season conditions, plants typically flower in mid-November in Southern California; under artificial long nyctoperiod/short photoperiod conditions, plants flower within about 8 to 8.5 weeks.

*Post-production longevity*.—Good post-production longevity; plants of the new Poinsettia maintain good substance and flower bract color for about four weeks under interior conditions; inflorescences persistent.

*Inflorescence diameter*.—About 33 cm.

*Inflorescence height (depth)*.—About 7.5 cm.

*Flower bracts*.—Quantity per inflorescence: About 22. Length, largest bracts: About 15.8 cm. Width, largest bracts: About 11.4 cm. Shape: Broadly lanceolate. Apex: Acuminate. Base: Obtuse. Margin: Entire; not lobed. Texture, upper and lower surfaces: Smooth, glabrous; veins prominent on lower surface. Aspect: Mostly horizontal to slightly drooping with development. Venation pattern: Pinnate, arcuate. Color: Developing or transitional bracts, upper surface: Close to 59A to 59B; along midvein, close to 139A. Developing or transitional bracts, lower surface: Close to 147B tinted with close to 185B. Fully expanded bracts, upper surface: Close to 53A; venation, close to 53A; color fading slightly closer to N34A with development. Fully expanded bracts, lower surface: Close to 53B; venation, close to 53B; color fading slightly closer to N34A with development. Bract petioles: Length: About 4.3 cm. Diameter: About 3 mm. Texture, upper and lower surfaces: Smooth, glabrous. Color, upper and lower surfaces: Close to 185A.

*Cyathia*.—Quantity per corymb: About 15. Length: About 1.1 cm. Width: About 6 mm. Shape: Ovoid. Texture: Smooth, glabrous. Color, immature: Close to 146A. Color, mature: Close to 146A to 146B.

*Nectaries*.—Quantity per cyathium: Typically one. Length: About 5 mm. Width: About 3 mm. Shape: Elliptical. Texture: Smooth, glabrous. Color: Close to 15A to 15B.

*Peduncles*.—Length: About 3 mm. Diameter: About 2 mm. Strength: Strong. Aspect: Mostly upright to slightly outwardly. Texture: Smooth, glabrous. Color: Close to 146B.

*Reproductive organs*.—Stamens: Quantity per cyathium: About five. Filament length: About 3 mm. Filament color: Close to 59A. Anther shape: Oval; bi-lobed. Anther length: About 1 mm. Anther color: Close to 59A. Amount of pollen: Scarce. Pollen color: Close to 9A. Pistils: Pistil development has not been observed on plants of the new Poinsettia.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER1295' as illustrated and described.

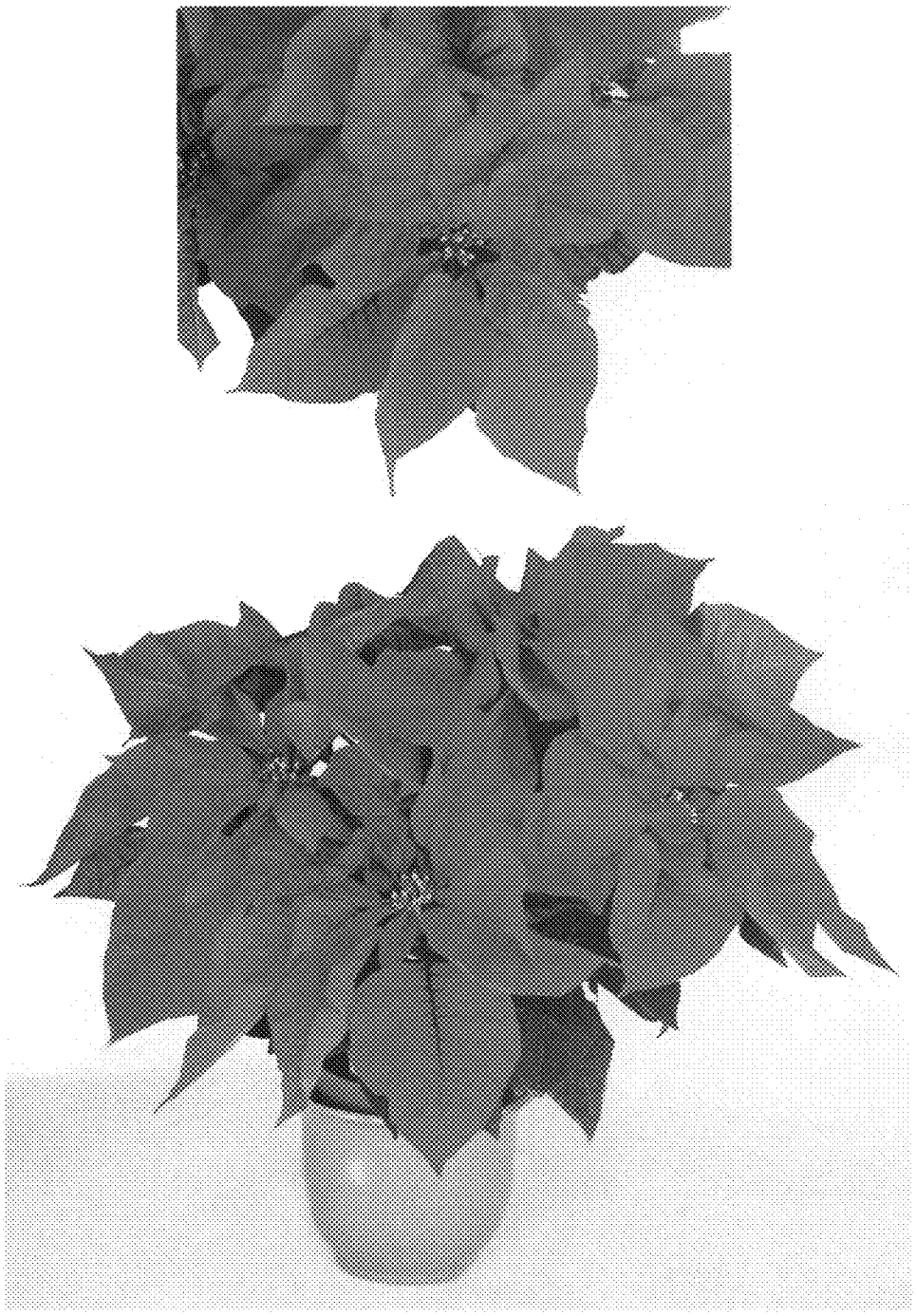

* * * * *